United States Patent [19]

Sato et al.

[11] 4,151,834

[45] May 1, 1979

[54] ULTRASONIC DIAGNOSTIC APPARATUS

[75] Inventors: Shigeru Sato, Yamato; Michiyoshi Uranishi, Tokyo, both of Japan

[73] Assignee: Tokyo Shibaura Electric Co., Ltd., Japan

[21] Appl. No.: 816,030

[22] Filed: Jul. 15, 1977

[30] Foreign Application Priority Data

Sep. 30, 1976 [JP] Japan .................................. 51-117557

[51] Int. Cl.$^2$ ............................................. A61B 10/00
[52] U.S. Cl. ................................... 128/660; 128/661; 73/619
[58] Field of Search .......................... 128/2 V, 2.05 Z; 73/618, 619; 318/560, 616–618, 661, 678, 686, 326

[56] References Cited

U.S. PATENT DOCUMENTS

| | | | |
|---|---|---|---|
| 2,769,949 | 11/1956 | Stratton | 318/326 |
| 3,403,671 | 10/1968 | Flaherty et al. | 128/2 V |
| 3,555,888 | 1/1971 | Brown | 128/2 V |
| 3,654,479 | 4/1972 | Catherin | 250/231 SE |
| 3,665,282 | 5/1972 | Skehan | 318/627 |
| 3,927,661 | 12/1975 | Takemura et al. | 128/2 V |
| 3,952,236 | 4/1976 | Hoover | 318/326 X |
| 3,974,826 | 8/1976 | Eggleton et al. | 128/2 V |
| 4,020,348 | 4/1977 | Turcotte et al. | 250/363 S |
| 4,034,744 | 7/1977 | Goldberg | 128/2 V |

OTHER PUBLICATIONS

Griffith, J. M. et al. "A Sector Scanner for Two-Dimensional Echocardiography," Circulation vol. XLIX, 6/74 pp. 1147–1152.

Primary Examiner—Robert W. Michell
Assistant Examiner—Francis J. Jaworski
Attorney, Agent, or Firm—Finnegan, Henderson, Farabow & Garrett

[57] ABSTRACT

An ultrasonic diagnostic apparatus comprises a probe having at least one electro-acoustic transducing element, a motor for imparting a sector motion to the probe, a pulse oscillator for energizing the electro-acoustic transducing element to generate ultrasonic pulses, and a signal processing circuit connected to receive from the electro-acoustic transducing element electric signals corresponding to the ultrasonic signals received by the probe and to process the electric signals so as to provide information on the living body being examined. The apparatus further comprises a first control circuit connected to receive first reference signals of a predetermined frequency and control the rotation of the motor according to the first reference signals, a second control circuit connected to receive second reference signals and control the rotation of the motor according to the second reference signals, and a switching circuit for connecting the first and second control circuits alternatively to the motor.

12 Claims, 8 Drawing Figures

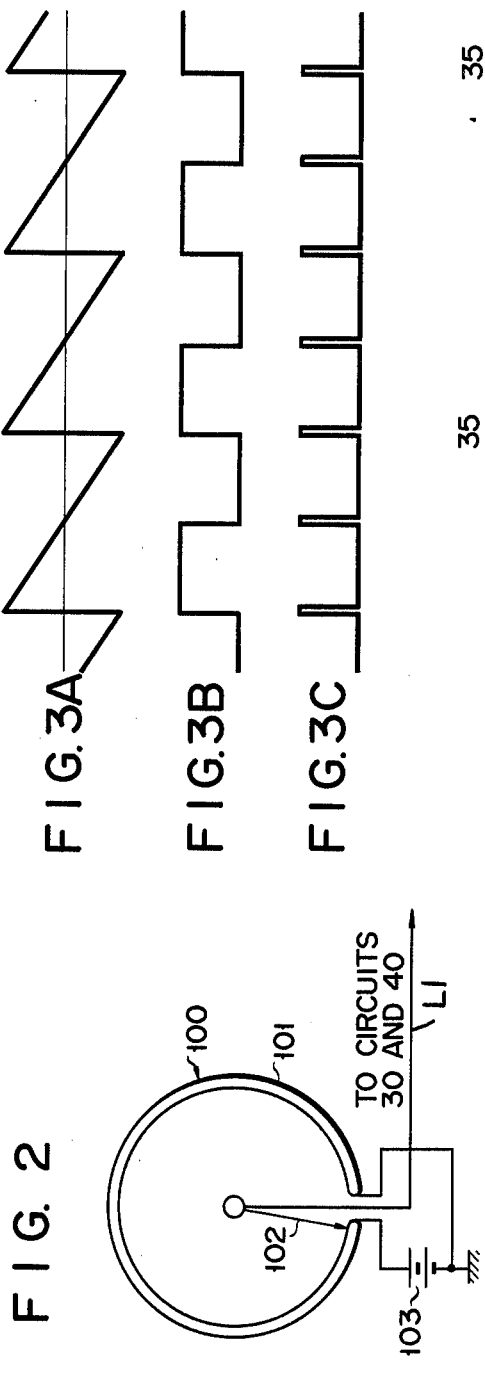

ically illustrated in FIG. 1.

ULTRASONIC DIAGNOSTIC APPARATUS

BACKGROUND OF THE INVENTION

This invention relates to an ultrasonic diagnostic apparatus for medical examination.

Hitherto known is an ultrasonic diagnostic apparatus which is provided with a high speed mechanical scanner. In the mechanical scanner the rotation of a motor is converted into a sector motion of an electro-acoustic transducer. That is, the electro-acoustic transducer of an ultrasonic probe is receiprocated along an arc so as to catch the entire image of a quickly moving organ. The electro-acoustic transducer is reciprocated as quickly as 30 times per second, thereby projecting a tomogram of an organ on the cathode ray tube. In clinical examination, it is desired that not only such a tomogram but also a graph showing the movement of a particular portion of an organ in a specific direction, e.g. ultrasonic cardiogram, should be obtained from the ultrasonic probe. The tomogram and such a graph are comparatively studied to give a more reliable diagnosis than otherwise. Thus, there has long been a need for an ultrasonic diagnostic apparatus which can provide not only a tomogram by sector-moving the probe and scanning an organ with an ultrasonic beam but also an ultrasonic cardiogram by fixing the probe to a specific direction.

SUMMARY OF THE INVENTION

Accordingly, the object of the invention is to provide an ultrasonic diagnostic apparatus which can obtain an ultrasonic cardiogram or kimogram of a living body as well as a tomogram of the living body.

According to an aspect of this invention, there is provided an ultrasonic diagnostic apparatus comprising a probe having an electro-acoustic transducer, drive means for moving the electro-acoustic transducer to reciprocate, means for urging the electro-acoustic transducer to generate an ultrasonic wave, a signal processing circuit for processing electric signals into which the electro-acoustic transducer has converted the ultrasonic wave received by the probe, first control means connected to receive first reference signals of a predetermined frequency and control the drive means according to the first reference signals thereby to reciprocate the electro-acoustic transducer at a predetermined speed, second control means connected to receive second reference signals and control the drive means according to the second reference signals, and a switching circuit for connecting the first and second control means alternatively to the drive means.

BRIEF DESCRIPTION OF THE DRAWING

FIG. 2 shows the angle detector used in the ultrasonic diagnostic apparatus illustrated in FIG. 1;

FIGS. 3A to 3C show the waveforms of signals generated at three points in the control circuits of the apparatus shown in FIG. 1;

FIGS. 4 and 5 show the ultrasonic cardiogram and kimogram obtained by the apparatus shown in FIG. 1, respectively; and FIG. 6 shows another angle detector for the ultrasonic diagnostic apparatus illustrated in FIG. 1.

DETAILED DESCRIPTION OF THE PREFERRED EMBODIMENTS

Figure 1:
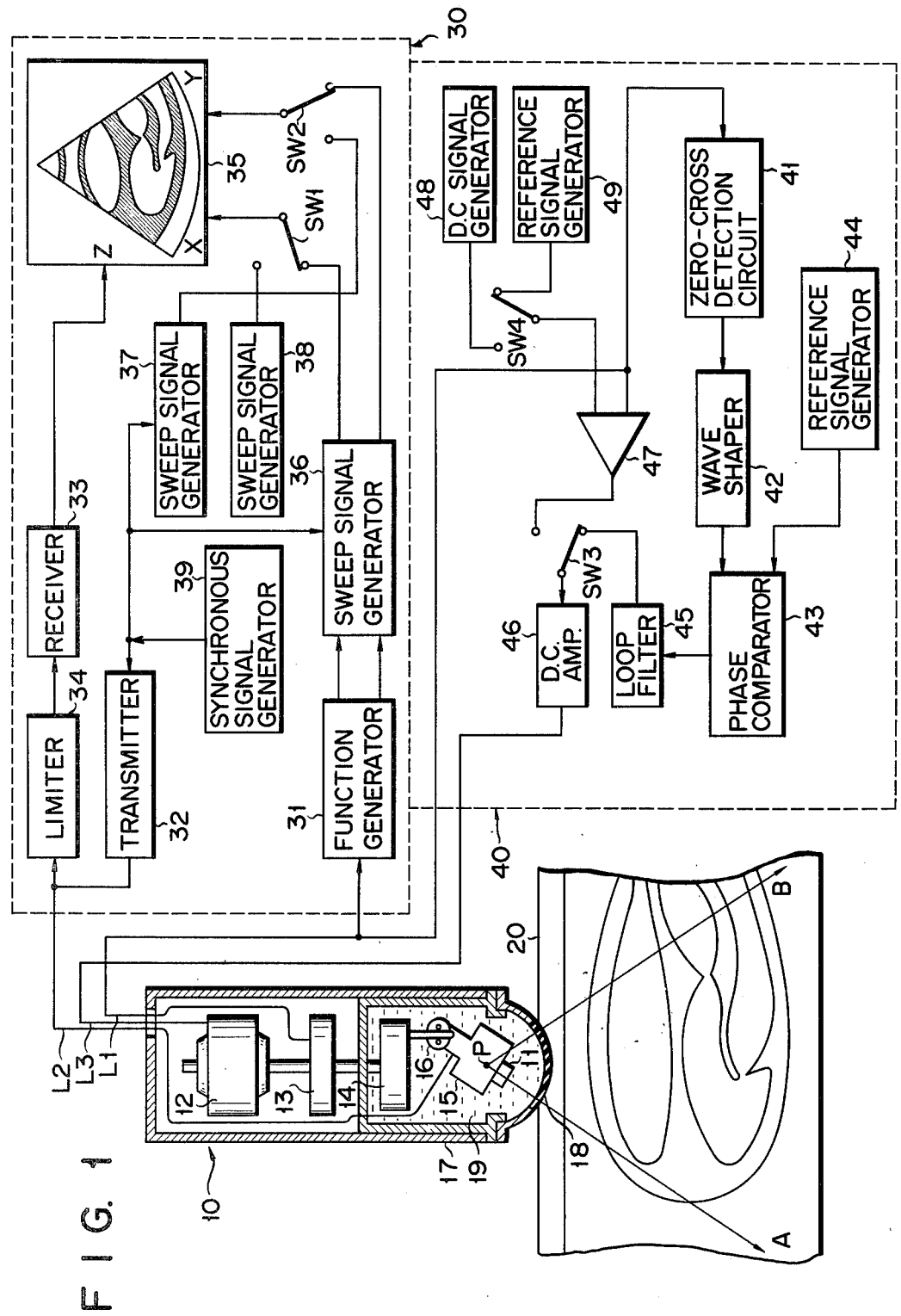
FIG. 1 shows the construction of an ultrasonic diagnostic apparatus according to this invention.

FIG. 1 is a diagram of an ultrasonic diagnostic apparatus. The apparatus comprises a mechanical scanning device 10, an electric signal transmitting and processing circuit 30 and a control circuit 40. The probe 11 of the scanning device 10 has at least one electro-acoustic transducing element and is adapted to generate an ultrasonic beam. The electric signal transmitting and processing circuit 30 is connected to urge the probe 11 to generate an ultrasonic beam, and to receive and process the electric signals corresponding to the ultrasonic signals reflected from a living body 20 which is schematically illustrated in FIG. 1.

The mechanical scanning device 10 is comprised of a DC servomotor 12, an angle detector 13 coupled to the shaft of the motor 12, a flywheel 14 coupled also to the shaft of the motor 12, a probe holder 15 for supporting the probe 11, and a coupling mechanism 16 for coupling the flywheel 14 to the probe holder 15. The angle detector 13 is adapted to detect the angle of rotation of the DC servomotor 12. The coupling mechanism 16 is constituted by, for example, a Scotch-yoke mechanism.

The coupling mechanism 16 converts the rotation movement of the flywheel 14 into a reciprocating motion, thereby to impart a sector motion to the probe holder 15 pivoted at point P. Thus, the upper end of the probe holder 15 is repeatedly swung substantially in the same plane. As a result, the probe 11 supported on the lower end of the holder 15 is reciprocated along an arc of a circle around point P. Reciprocated in this manner, the probe 11 emits the ultrasonic beam at any angle within the range indicated by arrows A and B.

The mechanical scanning device 10 has a case 17 whose lower end is covered with a flexible film 18 made of, for instance, silicone rubber. A smooth contact is therefore made between the scanning device 10 and the living body 20. The probe 11 is hermetically enclosed in a chamber 19, which is filled with a sound-coupling medium such as water or oil. Filled up with the medium, the chamber 19 provides a better sound transmission between the probe 11 and the living body 20 than otherwise.

The angle detector 13 is constituted by, for example, such a potentimeter 100 as illustrated in FIG. 2. The potentiometer 100 comprises a resistor 101, i.e. a ring of wire, and a slider 102. One end of the slider 102 is attached to the shaft of the motor 12 and swings as the shaft rotates, while the other end is made to slide on the resistor 101. Between the ends of the ring-shaped resistor 101, there is connected a power source 103. The slider 102 is connected through a line L1 to a function generator 31 of the signal transmitting and processing circuit 30 and a zero-cross detection circuit 41 of the control circuit 40.

When the angle of rotation of the motor 12 is 0°, the free end of the slider 102 remains in contact with the starting end of the resistor 101, i.e. the positive terminal of the power source 103. In this case, a maximum voltage is applied through the line L1 to both the signal transmitting and processing circuit 30 and the control circuit 40. As the motor 12 rotates, the voltage on the line L1 is gradually lowered in proportion to the angle of rotation. The lower voltage is applied to the circuits 30 and 40 through the line L1. When the motor 12 rotates substantially by 360°, the voltage on the line L1 is lowered substantially to 0 volt. If the motor 12 rotates a little further, the potentiometer builds up the maximum voltage again. Thus, as the motor 12 goes on rotating, the angle detector 13 produces an output voltage having such a sawtooth waveform as illustrated in FIG. 3A.

The signal transmitting and processing circuit 30 is provided with a transmitter 32 and a receiver 33. The transmitter 32 controls, through a line L2, the electro-acoustic transducing element and causes it to generate an ultrasonic beam which is emitted by the probe 11. The receiver 33 receives through the line L2 the electric signals which correspond to the ultrasonic wave detected by the probe 11. A limiter 34 is connected to the receiver 33, so that the input signals applied to the receiver 33 are little affected by the output signals from the transmitter 32. The output signals from the receiver 33 are supplied to the Z terminal of a display unit 35, e.g. a cathode ray tube.

The function generator 31 of the signal processing circuit 30 produces signals which represent the sine and cosine values of the scan angle $\theta$ as represented by the output voltage of the angle detector 13. These signals representing "sin $\theta$" and "cos $\theta$" are supplied to a sweep signal generator 36. The sweep signal generator 36 supplies an X signal and a Y signal to X and Y terminals, respectively, of the dislay unit 35 through switches SW1 and SW2, respectively. Further provided are sweep signal generators 37 and 38 which supply sweep signals to the X and Y terminals of the display unit 35 through the switches SW1 and SW2, respectively. A synchronous signal generator 39 supplies a synchronous signal of, for example, 3.6KHz to the transmitter 32 and to sweep signal generators 36 and 37, thereby establishing synchronism between the received signal supplied to the Z terminal of the display unit 35 and the signals supplied to the X and Y terminals thereof.

The zero-cross detection circuit 41 of the control circuit 40 detects the moment the output signal of the angle detector 13 crosses the zero level, and supplies to a wave shaper 42 an output signal having such a waveform as illustrated in FIG. 3B. The wave shaper 42 produces a pulse every time the output signal of the zero-cross detection circuit 41 has its level changed, as shown in FIG. 3C. The output signal of the wave shaper 42 can be described as a techometer signal and is supplied to one input terminal of a phase comparator 43. The other input terminal of the phase comparator 43 receives the output signal of a reference signal generator 44, which is, for example, a 60Hz pulse signal transformed from a synchronous signal generally used, for example in 8-millimeter cameras or monitor TV cameras. Thus, the phase of the output signal of the wave shaper 42 is compared with that of the reference signal from the reference signal generator 44.

The output signal of the phase comparator 43 is supplied through a loop filter 45 constituted by, for instance, a low pass filter and through a switch SW3 to a DC amplifier 46 for driving the motor 12. The output signal of the DC amplifier 46 is supplied to the motor 12 through a line L3. The switch SW3 is of the single-pole, double-throw type and has a movable contact arm connected to the input terminal of the DC amplifier 46, a first contact pole connected to the output terminal of the loop filter 45, and a second contact pole cnnected to the output terminal of a differential amplifier 47. One of the input terminals of the differential amplifier 47 receives the output signal of the angle detector 13. Connected to the other input terminal of the differential amplifier 47 is a single-pole, double-throw switch SW4 through which a DC signal generator 48 and a reference signal generator 49 are selectively connected to the other input terminal of the differential amplifier 47. The switch SW4 has a movable contact arm connected to the other input terminal of the differential amplifier 47, a first contact pole connected to the output terminal of the DC signal generator 48, and a second contact pole connected to the output terminal of the reference signal generator 49.

In the control circuit 40 shown in FIG. 1, the zero-cross detection circuit 41, wave shaper 42, phase comparator 43, reference signal generator 44, and DC amplifier 46 constitute a phase lock loop or first control loop. The DC signal generator 48 or reference signal generator 49, differential amplifier 47, and DC amplifier 46 constitute a second control loop. The operation of the switch SW3 permits the first and second control loops to be alternatively connected to the mechanical scanning device 10, thereby to control the sector motion of the probe 11.

There will now be described the operation of the ultrasonic diagnostic apparatus shown in FIG. 1.

To obtain an ultrasonic tomogram of the living body 20, the apparatus is operated in the following way. First, the switches SW1, SW2 and SW3 are set at the positions illustrated in FIG. 1. Thus, the output terminals of the sweep signal generator 36 are coupled to the X and Y terminals of the display unit 35, respectively, and the output terminal of the loop filter 45 is connected to the DC amplifier 46. Consequently, the motor 12 rotated as a speed which corresponds to the output signal of the DC amplifier 46. Driven by the motor 12, the probe 11 makes a sector motion to oscillate at the rate of, for example, abou 30 times per second. This means that each sweep of the ultrasonic beam which scans the living body 20 in a given direction within the range defined by arrows A and B, takes about one-sixtieth of second.

Each ultrasonic signal reflected from the living body and detected by the probe 11 is converted into an electric signal by the electro-acoustic transducing element. The electric signal thus obtained is supplied to the receiver 33 through the line L2 and the limiter 34. The receiver 33 produces a Z signal which represents the structure of the body portion along the ultrasonic beam corresponding to the ultrasonic signal. In the meantime, the output signal of the angle detector 13 is supplied to the function generator 31 through the line L1. The output signals "sin $\theta$" and "cos $\theta$" of the function generator 31 are supplied through the sweep signal generator 36 as X and Y signals to the display unit 35, respectively. The X and Y signals define the direction in which the ultrasonic beam has been emitted from the probe 11 and operate to control the beam deflection circuits of the display unit. The Z signal controls the beam intensity. Thus, the Z signal and the X and Y signals cooperate to form a tomogram of a limited portion of the living body. Finally, the tomogram is displayed on the screen of the display unit 35.

As mentioned above, the output signal of the angle detector 13 as shown in FIG. 3A is changed by the wave shaper 42 into such a signal as illustrated in FIG. 3C. The output signal of the wave shaper 42 is supplied to the phase comparator 43 and is compared with the output pulse of, for example, 60Hz from the reference generator 44. If no phase difference is found between these signals, the phase comparator 43 produces a DC voltage of a predetermined level. If the output signal of the wave shaper 42 is delayed with respect to the output signal of the reference signal generator 44, the phase comparator 43 supplies the DC amplifier 46 with a DC voltage of a higher level than the predetermined level through the loop filter 45 and the switch SW3 thereby elevates the DC output level of the DC amplifier 46 and increases the speed of the motor 12. On the other hand, if the output signal of the wave shaper 42 leads the signal from the reference signal generator 44, the phase comparator 43 supplies the DC amplifier 46 with a DC voltage of a lower level than the predetermined one thereby lowering the level output level of the DC amplifier 46 and decreasing the speed of the motor 12. In this way, the speed of rotation of the motor 12 is synchronized to the frequency of the output signal from reference signal generator 44. The probe 11 is therefore oscillated through a predetermined sector scan angle at a speed controlled by the output signal from reference signal generator 44.

To obtain an ultrasonic cardiogram of the living body 20 by applying an ultrasonic beam to the living body 20 from the probe 11 in a specific direction, the apparatus is operated in the following manner. First, the switches SW1 and SW2 are so set as to couple the sweep signal generators 38 and 37 to X and Y terminals respectively, of the display unit 35. The switch SW3 is set to couple the output terminal of the differential amplifier 47 to the input terminal of the DC amplifier 46, and the switch SW4 is set to couple the DC signal generator 48 to the input terminal of the differential amplifier 47. Then, the DC signal generator 48 is operated, for instance, by hand to supply a DC voltage of a desirable level to the input terminal of the differential amplifier 47.

The differential amplifier 47 compares the output signal of the DC signal generator 48 with the output signal of the angle detector 13. Its output signal level becomes 0 volt when the output level of the angle detector 13 equals that of the DC signal generator 48, whereby the motor 12 stops rotating. In other words, the motor 12 is stopped once it has been rotated to the angle which corresponds to the DC output voltage of the DC signal generator 48. Since the motor 12 is stopped at a predetermined angle position, the probe 11 is positioned at a specific angle with respect to the living body 20. Consequently, the probe 11 emits an ultrasonic beam in a specific direction. This direction can be changed by changing the DC output voltage of the DC signal generator 48. Thus, it is possible to display on the display unit 35 such ultrasonic cardiograms as shown in FIG. 4 which are obtained by directing the ultrasonic beam in a desired direction. In FIG. 4, time is plotted on the abscissa, and the depth of the probed parts in the living body 20 on the ordinate.

To obtain a kimogram, the probe 11 is driven to make a slow sector motion in the following manner. The switches SW1, SW2 and SW4 are set as illustrated in FIG. 1. Only the switch SW3 is so set as to couple the output terminal of the differential amplifier 47 to the input terminal of the DC amplifier 46. The differential amplifier 47 receives the output signal of the angle detector 13 and the output signal of the reference signal generator 49 which has a low frequency, for example 0.03 to 0.50Hz. Then, it produces an output signal which corresponds to the level difference between the input signals from the angle detector 13 and the reference signal generator 49. The output signal of the differential amplifier 47 is supplied to the DC amplifier 46. As a result, the DC amplifier 46 supplies to the motor 12 its output signal whose level changes at a rate as low as the frequency of the output signal from the reference signal generator 49. Supplied with such output signal of the DC amplifier 46, the motor 12 rotates slowly. Driven by the motor 12, the probe 11 makes a slow sector motion to reciprocate. During the sector motion, the probe 11 emits an ultrasonic beam to provide such a kimogram as illustrated in FIG. 5.

The kimogram may also be obtained if the switch SW4 is so set as to connect the DC signal generator 48 to the differential amplifier 47 and then the DC signal generator 48 is manually operated to elevate or lower gradually the level of its DC output signal. In this case, the ultrasonic cardiogram of each probed part of the living body 20 can be observed only if the DC output level of the DC signal generator 48 is changed extremely slowly.

This invention is not limited to this embodiment, but may be practised in many other modifications. For example, the angle detector 13 may be constituted by such an encoder 110 as shown in FIG. 6, instead of such a potentiometer 100 as illustrated in FIG. 2. The encoder 110 comprises a disc 111 driven by a motor 12 and having a plurality of slots 116 which are radially extending and equally spaced from each other, a light source 112 positioned on one side of the disc 111, and a light detector 113, e.g. a phototransistor, positioned on the other side of the disc 111. In this case, the light detector 113 produces one voltage pulse each time it detects light from the light source 112 through the slot 116. This pulse signal is supplied to the phase comparator 43 of the control circuit 40. It is further supplied to a ring counter 114, which is reset to zero count upon reaching the count corresponding to the number of slots of the disc 111, that is, upon completion of each 360°-turn of the disc 111. The output count signal of the ring counter 114 is converted into an analog signal by a digital-analog converter 115. The analog signal thus obtained is fed to the function generator 21 of the signal processing circuit 30 and to the differential amplifier 47 of the control circuit 40.

Where the encoder 110 is employed as angle detector 13, the ring counter 114 and the digital-analog converter 115 are required for producing the sawtooth output signal, as illustrated in FIG. 3A. In this case, however, the wave shaper 42 and the zero-cross detection circuit 41 can be omitted. Since the encoder 110 supplies the phase comparator 43 with pulse signals which usually have a higher frequency than that of the signals produced by such a potentiometer as shown in FIG. 2, the synchronous control of the motor 12 is carried out more stably and reliably.

Further, the disc 111 may be provided with a plurality of radially extending mirrors, instead of a plurality of slots. In this case the light source 112 and the light detector 113 are disposed on the same side of the disc 111. The light from the light source 112 is reflected from the mirror, and the light detector 113 will successively catch the light reflected from the mirrors as the disc rotates.

What we claim is:
1. An ultrasonic diagnostic apparatus comprising:
probe means having an electro-acoustic transducer,
servo-motor means for driving said electro-acoustic transducer to oscillate through a predetermined angle range, means for generating an electric signal to be supplied to said electro-acoustic transducer thereby causing said probe to emit an ultrasonic wave toward an object to be examined, means for processing electric signals into which said electro-acoustic transducer has converted the ultrasonic wave received by said probe, said processing means including means for selectively displaying tomogram and cardiogram images of the object, means for generating a first reference signal, means for generating a second reference signal, means for producing a position signal indicative of the angular position of said probe means, first servo control means for controlling the speed of said servo-motor means according to the phase difference between said first reference signal and said position signal, whereby said probe means is driven to oscillate at a controlled velocity and said means for processing is conditioned to display a tomogram image of the portion of said object included in said angle range, second servo control means for controlling the shaft position of said servo-motor according to the level difference between said second reference signal and said position signal, whereby said probe means is driven to a position represented by the level of said second reference signal and said means for processing is conditioned to display a cardiogram image of the portion of said object located at said position, and switching means for coupling said first and second servo control means selectively to said servo-motor means to condition said processing means to display either said tomogram or said cardiogram image, respectively.

2. An ultrasonic diagnostic apparatus according to claim 1, wherein said second servo control means includes differential amplifier means for comparing said second reference signal with said position signal thereby to supply to said drive means an output signal which corresponds to the difference between the compared signals.

3. An ultrasonic diagnostic apparatus according to claim 2, wherein said position signal producing means comprises a potentiometer which has a slider driven by said drive means and which generates a position signal corresponding to the angle at which said probe is inclined.

4. An ultrasonic diagnostic apparatus according to claim 2, wherein said position signal producing means comprises a rotary encoder including a light source, a disc driven by said servo-motor means and having a plurality of light directing means arranged in the radial direction of the disc and angularly spaced from one another, and a light detector for generating output pulses in response to said light coming from said light source and directed by said light directing means, and said second servo control means includes means adapted to receive the output pulses from the light detector and to supply to said differential amplifier means an output signal the level of which corresponds to the number of output pulses generated by the light detector.

5. An ultrasonic diagnostic apparatus according to claim 4, wherein said plurality of light directing means are a plurality of slots formed in said disc, and said light source and light detector are arranged to face each other with said disc disposed therebetween.

6. In an ultrasonic diagnostic apparatus including probe means having an electro-acoustic transducer for emitting an ultrasonic wave, a servo-motor for driving said transducer through a predetermined scan sector including an object to be examined, and processing means for detecting reflected portions of said ultrasonic wave and for processing electric signals representing said reflected portions to display tomogram and cardiogram images of said object, means for controlling the operation of said servo-motor comprising, in combination:

means coupling said servo-motor to said probe such that unidirectional rotation of the shaft of said motor drives said transducer to traverse said scan sector in an oscillating scan motion;

means for generating a position signal in response to the motion of said transducer, said position signal having a level representing the position of said transducer in said scan sector;

means for generating a tachometer signal having a frequency proportional to the angular velocity of said servo-motor;

first servo control means responsive to said tachometer signal and to a first reference signal for generating a first motor control signal which, when applied to said servo-motor, produces continuous rotation of said motor at a controlled velocity, whereby said transducer is continuously scanned through said scan sector and said processing means is conditioned to display a tomogram image of said object;

second servo control means responsive to said position signal and to a second reference signal for generating a second motor control signal which, when applied to said servo-motor, positions said motor shaft at a predetermined angular position in said scan sector, whereby said processing means is conditioned to display a cardiogram image of a selected portion of said object; and switching means for selectively applying said first and second motor control signals to said servo-motor to control said processing means to display either tomogram or cardiogram images.

7. An ultrasonic diagnostic apparatus comprising:

a probe having an electro-acoustic transducer, drive means for oscillating said electro-acoustic transducer, electric signal generating means for supplying an electric signal to said electro-acoustic transducer thereby causing said probe to emit an ultrasonic wave, a signal processing circuit for processing electric signals into which said electro-acoustic transducer has converted the ultrasonic wave received by said probe, a first reference signal generator for generating a first reference signal of a predetermined frequency, first control means adapted to receive said first reference signal and to generate a first drive signal for controlling said drive means according to said first reference signal thereby to drive said electro-acoustic transducer at a predetermined speed, information signal generating means connected to said drive means for generating an information signal representing the position of said probe, a D.C. signal generator for generating a position reference signal, a second reference signal generator for generating a second reference signal of a frequency lower than that of said first reference signal, second control means including differential amplifier means for comparing a signal supplied to a first input thereof with the output signal from said information signal generating means, thereby supplying a second drive signal which corresponds to the difference between said compared signals, first switching means for selectively coupling either said position reference signal from said D.C. signal generator or said second reference signal to said first input of said differential amplifier means, and second switching means for selectively coupling either the output from said differential amplifier or the output from said first control means to said drive means, thereby allowing either said first drive signal or said second drive signal to control the movement of said electro-acoustic transducer, whereby said transducer can, through operation of said first and second switching means, be driven to oscillate at a first speed under control of said first drive signal, or at a second lower speed under control of said second drive signal, or can be moved to a selected position under control of said position reference signal.

8. An ultrasonic diagnostic apparatus according to claim 7, wherein said information signal generating means comprises a potentiometer which has a slider driven by said drive means and which generates said information signal corresponding to the angle at which said probe means is inclined.

9. An ultrasonic diagnostic apparatus according to claim 7, wherein said information signal generating means includes a rotation angle detector, said drive means comprises a D.C. servo-motor the rotation angle of which is detected by said rotation angle detector, and said first control means includes a phase comparator for comparing the output signal of the rotation angle detector with said first reference signal, whereby said first drive signal is a D.C. signal having a level corresponding to the phase difference between the compared signals.

10. An ultrasonic diagnostic apparatus according to claim 9, wherein said information signal producing means comprises a rotary encoder having a light source, a disc attached to the shaft of said D.C. servo-motor and having a plurality of light directing means arranged in the radial direction of said disc and angularly spaced from one another, and a light detector for supplying output pulses in response to the light coming from said light source and directed by said light directing means, said output pulses being phase-compared with said first reference signal.

11. An ultrasonic diagnostic apparatus according to claim 10, wherein said second servo control means includes means for generating, in response to the output pulses of said light detector, an output signal having a level corresponding to the number of output pulses generated by the light detector, said output signal being compared with said second reference signal to determine said level difference.

12. An ultrasonic diagnostic apparatus according to claim 10, wherein said plurality of light directing means include a plurality of slots formed in said disc, and said light source and light detector are arranged to face each other with said disc disposed therebetween.

* * * * *